United States Patent
Bruza et al.

(10) Patent No.: US 12,036,421 B2
(45) Date of Patent: Jul. 16, 2024

(54) SYSTEMS AND METHODS FOR FLASH THERAPY

(71) Applicant: THE TRUSTEES OF DARTMOUTH COLLEGE, Hanover, NH (US)

(72) Inventors: Petr Bruza, Lebanon, NH (US); Brian Pogue, Hanover, NH (US); Ramish Ashraf, Hanover, NH (US); Rongxiao Zhang, Hanover, NH (US); David Gladstone, Norwich, VT (US); Megan Clark, Hanover, NH (US); Roman Vasyltsiv, Staten Island, NY (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 18/563,813

(22) PCT Filed: May 25, 2022

(86) PCT No.: PCT/US2022/030837
§ 371 (c)(1),
(2) Date: Nov. 22, 2023

(87) PCT Pub. No.: WO2022/251300
PCT Pub. Date: Dec. 1, 2022

(65) Prior Publication Data
US 2024/0173569 A1 May 30, 2024

Related U.S. Application Data

(60) Provisional application No. 63/193,030, filed on May 25, 2021.

(51) Int. Cl.
*A61N 5/10* (2006.01)

(52) U.S. Cl.
CPC ......... *A61N 5/1031* (2013.01); *A61N 5/1049* (2013.01); *A61N 5/1067* (2013.01); *A61N 5/1071* (2013.01); *A61N 2005/1059* (2013.01)

(58) Field of Classification Search
None
See application file for complete search history.

(56) References Cited

U.S. PATENT DOCUMENTS

| | | | |
|---|---|---|---|
| 10,569,105 B2 * | 2/2020 | Kilby | A61N 5/1075 |
| 2007/0127622 A1 * | 6/2007 | Main | A61N 5/1049 378/64 |

(Continued)

FOREIGN PATENT DOCUMENTS

| | | |
|---|---|---|
| WO | WO 2000/07930 A1 | 12/2000 |
| WO | WO 2000/079302 A1 | 12/2000 |

(Continued)

OTHER PUBLICATIONS

International Patent Application No. PCT/US2022/030837 International Search Report and Written Opinion dated Sep. 2, 2022, 11 pages.

*Primary Examiner* — Hoon K Song
(74) *Attorney, Agent, or Firm* — Cozen O'Connor

(57) ABSTRACT

A system for delivering ultra-high dose rate irradiation to a target area of a patient, includes a pulsed charged-particle source along a beam axis; a collimator for shaping the beam of radiation; one or more cameras for imaging the target area of the patient; and a dosimetry controller for providing control signals to the charged-particle source one or more dosimeters positioned between an output of the charged-particle source and the collimator in beam fringes for measuring a radiation dosage provided by each pulse; and a beam scanning coil positioned between the collimator and the patient for directing the shaped beam. The dosimetry controller receives feedback from the one or more dosim- (Continued)

eters and provides control signals to the particle source and the beam scanning coil that modulate final pulses in the series of pulses in real-time.

17 Claims, 3 Drawing Sheets

(56) References Cited

U.S. PATENT DOCUMENTS

| | | |
|---|---|---|
| 2015/0196779 A1 | 7/2015 | Tonner |
| 2018/0036557 A1* | 2/2018 | Yoshimizu ............ A61N 5/1049 |
| 2020/0061391 A1* | 2/2020 | Krishnaswamy .... A61N 5/1071 |
| 2020/0196428 A1 | 6/2020 | Ryding et al. |
| 2021/0001153 A1* | 1/2021 | Pogue ..................... G01T 7/005 |

FOREIGN PATENT DOCUMENTS

| | | |
|---|---|---|
| WO | WO 2021/05053 A1 | 3/2021 |
| WO | WO 2021/050535 A1 | 3/2021 |

* cited by examiner

SYSTEMS AND METHODS FOR FLASH THERAPY

CROSS-REFERENCE TO RELATED APPLICATIONS

This application is a national phase application based on International Application No. PCT/US2022/030837, filed May 25, 2022, which claims priority to Provisional Patent Application No. 63/193,030 filed May 25, 2021, titled "Systems and Methods for Accurate Flash Therapy," both of which are incorporated herein by reference.

GOVERNMENT RIGHTS

This invention was made with government support under grant no. R01 EB023909 awarded by the National Institutes of Health. The government has certain rights in the invention.

FIELD

The present application relates to the fields of radiotherapy and dosimetry. In particular, the present application relates to systems and methods that will prevent erroneous delivery of a charged particle beam.

BACKGROUND

Pre-clinical studies of ultra-high dose rate irradiation therapy have demonstrated a striking reduction of normal tissue toxicities commonly associated with conventional radiotherapy while also maintaining tumor control, a phenomenon called the FLASH effect. Recently, a first human patient was treated with FLASH and a first human trial is underway indicating the widespread interest in FLASH. The premise of FLASH is to deliver whole dose radiotherapy or fractions at much higher dose rates than with conventional radiotherapy, typically above 40 grays/second (Gy/s) as compared to 0.01 Gy/s in a conventional mode. Ultra-high dose rate irradiation may be used with electrons, protons, and X-rays.

There are numerous challenges associated with the rapid nature of FLASH delivery, particularly with regard to dose feedback systems and interlock circuitry. Current beam monitor dosimeters are either not useful in high dose rate regimes due to strong non-linearity and/or signal to noise issues, they may experience dose-induced damage when subjected to ultra-high dose rate beams, or they are not fast enough to react on a single pulse, millisecond basis. In addition, while delivering the radiation dose of an entire therapy session with a single fraction lasting less than a second is typically seen as an advantage of FLASH, it imposes new and extreme requirements from the aspects of safety and patient positioning. In standard fractionated delivery, positioning, motion, or anatomy change errors are usually accounted for during planning and they tend to average out over multiple days of treatment. However, a small deviation in patient position in FLASH can have an impact on a patient's health that is orders of magnitude more severe than with conventional radiotherapy.

Prior art systems and methods for ultra-high dose rate irradiation are not capable of reacting to anatomical shifts that may occur anytime between patient alignment and the end of beam delivery, for example, shifts due to a non-compliant patient, inadvertent movement, breathing, etc. Further, in clinical linear accelerators (LINACs), the feedback mechanisms are based on averaged readouts over extended periods of time (for example 50 ms. in Varian LINACs). This feedback mechanism is too slow for FLASH. Also, current surface guided radiotherapy devices are not useful because the field of view is typically obstructed by the presence of an electron applicator.

SUMMARY OF THE EMBODIMENTS

In a first aspect, a system for ultra-high dose rate irradiation includes a particle source for providing a beam of radiation in a series of pulses; one or more scintillator detectors at an output of the particle source to measure beam output and symmetry in real-time; and a controller for receiving an input from the one or more scintillator detectors and providing control signals to the particle source.

In a second aspect, a method of ultra-high dose rate irradiation includes providing a series of charged particle pulses; measuring the radiation dosage in each pulse; determining a difference in the radiation dosage between a delivered dose and a prescribed dose; and if the difference is smaller than a single pulse radiation dosage, applying a scaling factor to the width or intensity of the following pulse.

DETAILED DESCRIPTION

Figure 1:
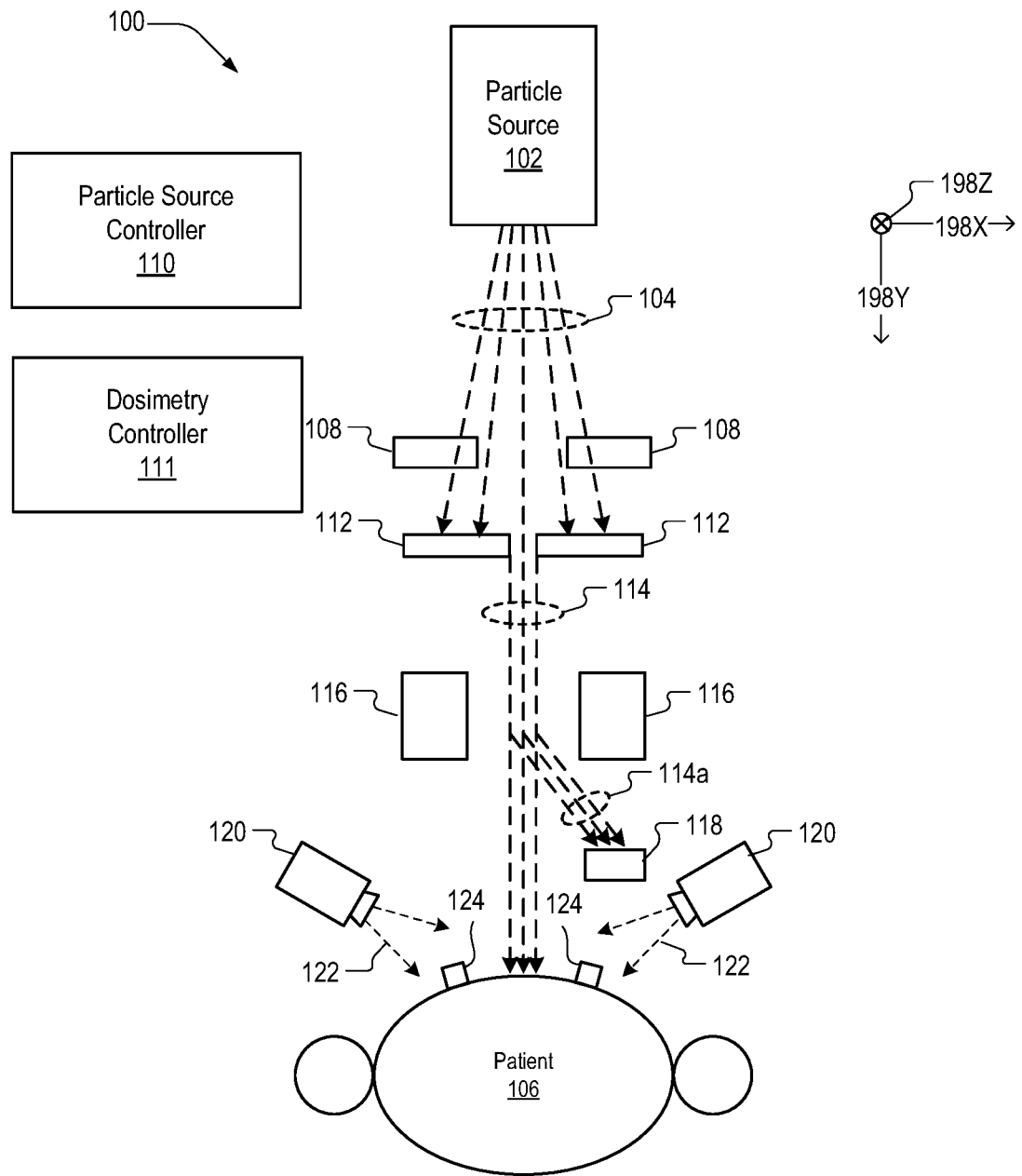
FIG. 1 is a block diagram of a system for delivering ultra-high dose rate irradiation therapy, in embodiments.

FIG. 1 depicts a system 100 for delivering ultra-high dose rate irradiation, or FLASH therapy, to a target area of a patient while preventing erroneous delivery of the radiation beam in terms of total dose and beam position. Systems and methods are described herein in the context of electron beams, but more generally are applicable to all types of charged particle beams such as electrons or protons, and X-ray beams. FIG. 1 includes a coordinate system indicated by x-axis 198X, y-axis 198Y and z-axis 198Z each of which are orthogonal to the others. As used herein a beam axis is parallel toy-axis 198Y and an image target plane is parallel to the x-z plane formed by x-axis 198X and z-axis 198Z.

Radiation source 102 outputs charged particle beam 104 towards a target area in an image target plane of patient 106 along a beam axis parallel to y-axis 198Y. In embodiments, particle source 102 may be a linear accelerator (LINAC) or synchro-cyclotron and particle beam 104 represents all beam types as described above. A fringe of particle beam 104 passes through dosimeter 108 which monitors the beam dose and provides feedback to particle source controller 110. In embodiments, particle source controller 110 includes processing, memory, input/output, and communication devices as necessary to accomplish the methods described herein.

System to Monitor High Dose Rate Output and Symmetry

In embodiments, dosimeter 108 may include a scintillator, which is a material that luminesces in response to radiation. Scintillators are typically linear across a large range of dose rates, thereby being ideal dose detectors for FLASH beam monitoring. In embodiments, a plurality of scintillator detectors is used at the beam output port of particle source 102 and positioned so that they measure doses in the fringe or an outer region of the beam 104 that is not used for treatment; in embodiments this outer region of the beam 104 is blocked by collimator 112, the collimator allowing an inner portion of the beam as shaped beam 114. In embodiments, dosimeter 108 may be a combination of a scintillator and photosensors or cameras (not shown) to detect light emitted by the scintillator; readings of light emitted by the scintillator are used to determine current and total radiation dose. Scintillator output is converted to dose using standard calibration mechanisms, allowing particle source controller to determine absolute beam output and symmetry in real-time. This beam output measurement may be used in methods described herein.

Scintillator Dosimeter Optimized for Ultra-High Dose Rate

In embodiments disclosed herein, dosimeter 108 may include an optical liquid cell filled with liquid scintillator solution, where the concentration and volume of the liquid scintillator are optimized for maximal signal and dose-rate independence while recording and reporting a time, an amplitude and a width of each individual pulse of the radiation beam. In an embodiment, the scintillator is a fluorescein solution. In another embodiment, the scintillator is a quinine solution. The optical liquid cell may be coupled to a light sensing detector (photodiode or photomultiplier tube) using an optical fiber. In an embodiment, this fiber is a hollow fiber with metal-coated walls, in order to minimize Cherenkov signal or other stray light contamination of scintillation light from the optical liquid cell. A method of dual wavelength readout may be utilized to cancel out any remaining Cherenkov signal contamination.

Fringes of beam 104 passes through dosimeter 108 while the body of beam 104 enters collimator 112, which may include adjustable shielding shapes configured to determine a shape of beam 104 to form shaped beam 114. In embodiments, any type of collimator that is capable of shaping ultra-high dose rate irradiation may be used. As shown in FIG. 1, portions of beam 104 passing through dosimeter 108 are blocked by collimator 112 and thus, not used in treatment of patient 106.

In embodiments, shaped beam 114 is steered using beam scanning coil 116 before application to patient 106.

Dosimeter 108 reports time, amplitude (or intra-pulse radiation dose), and pulsewidth of detected radiation pulses of the radiation beam to dosimetry controller 111 where these pulses are integrated and scaled according to a calibration function to provide a running total of radiation dose throughout the session. In some embodiments, cameras 120 also report Cherenkov images to dosimetry controller 111 where they are processed to provide a running total of radiation dose received by the patient throughout the treatment session.

Dosimetry Controller

Figure 2:
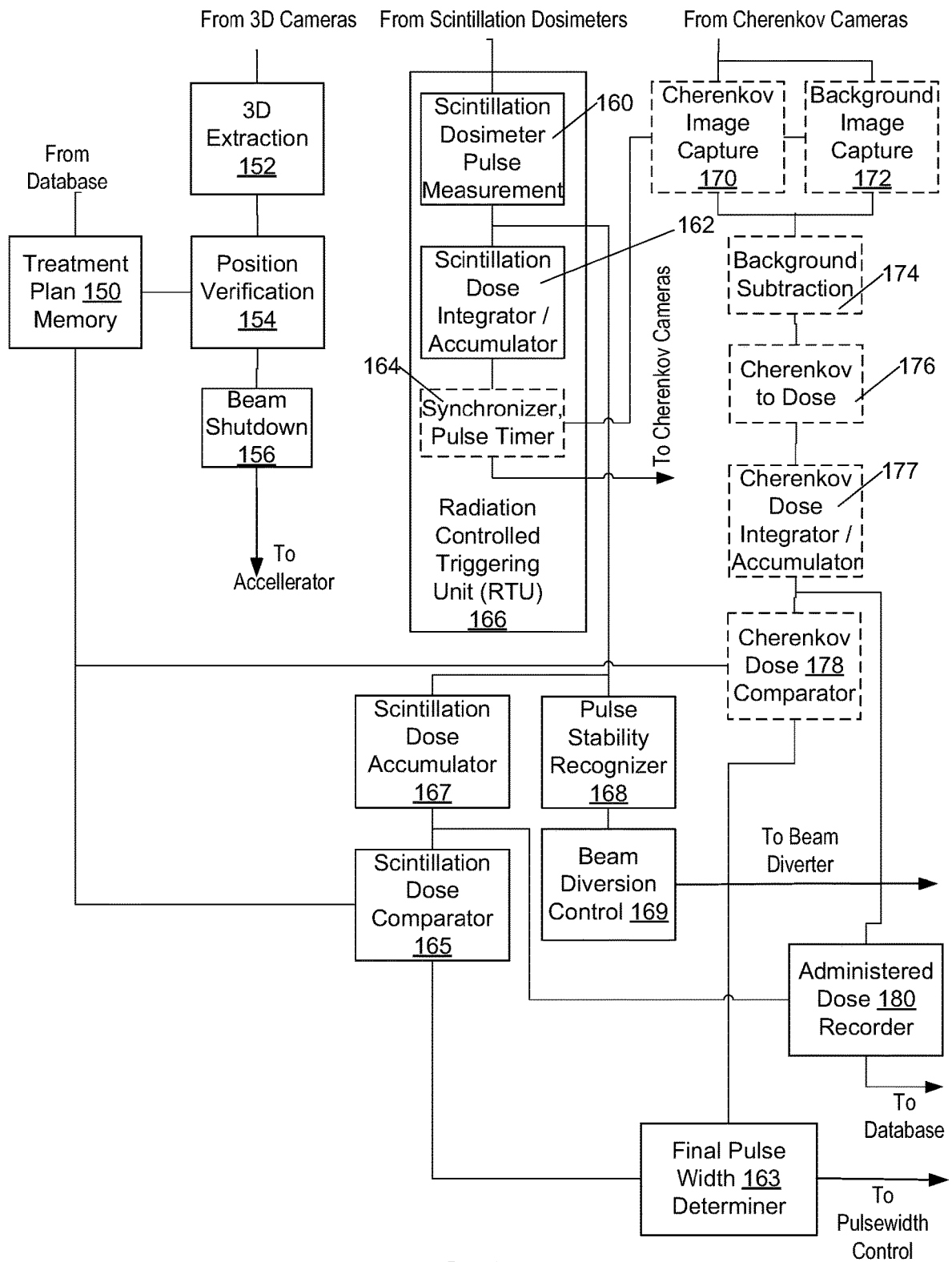
FIG. 2 is a functional block diagram illustrating some of the functions of a dosimetry controller of FIG. 1.

Further details of dosimetry controller 111 are shown in FIG. 2. In an embodiment, dosimetry controller 111 has a treatment plan memory 150 that is loaded from a patient database with relevant portions of a treatment plan. In addition to portions loaded into the dosimetry controller, the treatment plan also includes configuration settings for collimator 112 and for particle source 102 that in most embodiments is a pulsed particle accelerator such as a linear accelerator, a cyclotron, or a synchrotron. Relevant portions of the treatment plan incorporated into treatment plan memory 150 include anticipated Cherenkov shapes and limit dosages, anticipated scintillation limit dosage, fiducial locations relative to patient position, expected patient position, and expected beam energy and beam shape. Locations of all cameras 120 and locations and efficiencies of all scintillation dosimeters 108 are also known to dosimetry controller 111, although these locations and efficiencies may be constant for many treatment plans.

Pairs of 3D imaging cameras 120 are coupled through 3D surface extraction block 152 to position verification block 154, position verification block 154 is configured to compare extracted surfaces of patient 106 to expected patient and fiducial locations from treatment plan memory 150 and, if these differences exceed limits, beam shutdown logic 156 may be activated to discontinue or prevent radiation treatment of patient 106.

Scintillation dosimeters 108 are coupled to a scintillation pulse measurement unit 160 of dosimetry controller 111 where time, pulse height, and width are measured for each pulse of detected scintillation, these height and width being proportional to radiation intensity and duration or width of each pulse of beam 104 and their product proportional to radiation dose administered by each pulse. These heights and widths are multiplied together and totalized in scintillation dose integrator/accumulator 162 to provide signals representing radiation dose administered by the most recent pulse and a running total of radiation dose. In some embodiments, the time and pulse widths are also fed to an optional synchronizer and pulse timer unit 164 where gating signals are prepared for cameras of cameras 120 that are capable of imaging Cherenkov radiation, the combination of scintillation pulse measurement unit 160 and synchronizer and pulse timer unit 164 being known herein as a radiation-controlled triggering unit 166.

Scintillation dosimeter pulse time, height, and width are fed to a pulse stability recognizer 168 that recognizes when beam 104 pulses have become reasonably consistent in intensity and duration after particle source 102 startup because many types of accelerators that may be used as particle source 102 provide inconsistent pulses for a brief time after they are turned on. Until scintillation dosimeter pulses are recognized as stable by stability recognizer 168, beam diversion control 169 holds beam diverter and beam scanning coil 116 activated so shaped beam 114a is diverted into beam dump 118; after the pulses are recognized as consistent, shaped beam 114 is allowed to reach patient 106 and scintillation dose integrator/accumulator 167 is permitted to integrate and totalize radiation dose administered to patient 106.

Radiation dose logged by scintillation dose integrator/accumulator 167 is compared by scintillation dose comparator 165, together with dose administered by the most recent pulse of beam 104 as computed from beam pulse width and height, to planned dose information in treatment plan memory 150, when a sum of dose administered to patient 106 by the most recent pulse of beam 104 plus logged dose from scintillation dose integrator/accumulator 167 meets or exceeds planned dose, final pulse width determiner 163 computes a desired width for a final radiation pulse and provides a pulsewidth control signal to particle source 102.

In embodiments having cameras capable of imaging Cherenkov radiation among cameras 120, images from those cameras timed during pulses of shaped beam 114 are captured by Cherenkov image capture unit 170, and background images from those cameras, timed before or significantly after but not during pulses of the shaped beam 114 are captured by background image capture unit 172. A background subtraction unit 174 then corrects Cherenkov images for background room lighting and other stray lighting such as pilot lights and instrument lights around patient 106 into corrected Cherenkov images. The corrected Cherenkov images are converted to dosage maps of charge particles as administered to the patient 106 by a dose converter 176 and integrated or accumulated by Cherenkov dose map integrator accumulator 177 before being compared to a planned dose map portion of the treatment plan in treatment plan memory 150 by a Cherenkov dose map comparator 178. While flash treatment generally is performed in seconds to a few minutes to overwhelm DNA repair mechanisms in tissue, the pulses of the particle beam may in some embodiments be spread out over enough time that a compared dose map is ready in time for the final particle beam pulse, in these embodiments the final pulse width determiner 163 may use compared dose map in determining a width for a final pulse of shaped beam 114 to be emitted by particle source 102. Since this width of the final pulse is computed while treatment is proceeding, and pulses are cut off according to accumulated dose, the final pulses and final pulse width are referred to as computed in real time.

Both logged dose from scintillation dose integrator/accumulator 167 and accumulated Cherenkov dose map are recorded in a patient database by an administered dose recorder 180.

Beam Interruption System

In standard LINACs, a large variation in beam output is acceptable over a few initial pulses, before the LINAC reaches equilibrium and becomes stable within prescribed dose-per-pulse fluctuation, typically 3-5% of nominal beam output. In FLASH therapy, this equilibrium is typically reached too late throughout the treatment, as only several pulses are planned to be delivered. In embodiments, beam scanning coil 116 diverts shaped beam 114 as steered shaped beam 114a to beam dump 118 during an initial phase of beam output, or a ramp-up period of particle source 102, by electromagnetically diverting shaped beam 114. Once equilibrium and beam output stability has been reached, shaped beam 114 is then steered by beam scanning coil 116 away from beam dump 118 to a targeted area on patient 106. This re-direction happens between two beam pulses to avoid unintended irradiation of equipment and/or patient.

Cameras 120 are used to detect patient motion, and in some embodiments to measure and map radiation doses received by the patient by quantifying and imaging Cherenkov radiation, and in some embodiments scintillation emissions, generated within and emitted from the patient as the beam interacts with tissue of the patient. In embodiments, cameras 120 may operate using a variety of spectrums. To avoid camera damage, gated electronic cameras 120, are positioned outside shaped beam 114 with a general field of view 122 of the patient; cameras 120 are aligned such that field of view 122 includes a view of most or all of the treatment zone including a view of a surface of patient 106 that may be positioned within the treatment zone. The position of cameras 120 and their field of view 122 as shown in FIG. 1 are for purposes of illustration; more or fewer cameras may be used, and they may be placed in positions other than those shown in FIG. 1. In embodiments, cameras 120 may include optical or infrared three-dimensional cameras 120 for tracking patient location and movement. In embodiments, cameras 120 include intensified charge-coupled device (ICCD) camera, image-intensified CMOS (ICMOS) camera or an electronically-gated, sensitive, CMOS (EGCMOS) camera, configured to image Cherenkov radiation. In embodiments, cameras 120 may also include CMOS cameras placed in a 3-D camera setup to detect or monitor patient position and movement.

Where cameras 120 include cameras configured to image Cherenkov radiation, a processor of dosimetry controller 111 is configured to use images of Cherenkov radiation emitted by tissue of the patient to map radiation dose administered to the patient, to compare the mapped radiation dose administered to the patient to a treatment plan, and provide feedback to controller 110 to disable further treatment when either mapped radiation dose as administered to the patient, or integrated dosimeter 108 pulses, exceeds mapped radiation dose specifications or raw beam limitations of the treatment plan. Mapped radiation dose may also be displayed to a treating physician to determine if administered treatment was adequate to cover an entire tumor, or whether an additional treatment is required.

Cameras 120 may include several cameras each adapted to detect light from Cherenkov emissions and/or light of ultraviolet (UV), visible or near infrared (NIR) spectrums.

One or more of cameras 120 may be focused on target fiducials 124 in the region of the treatment zone. Target fiducials 124 may be artificial or biological as explained in more detail below. The locations of target fiducials 124 as shown in FIG. 1 are for purposes of illustration; more or fewer target fiducials 124 may be used, and they may be placed in positions other than those shown in FIG. 1.

Particle source controller 110 receives feedback and/or provides control signals (not shown) to particle source 102, dosimeter 108, collimator 12, cameras 120 and beam scanning coil 116. Other devices may also be coupled to particle source controller 110. Connections between particle source controller 110 may be wired or wireless.

Method of Real-Time Feedback Control

In embodiments, ultra-high dose rate irradiation, or FLASH therapy, delivers whole dose radiotherapy or fractions at much higher dose rates than conventional radiotherapy. For example, FLASH therapy dose rates are typically above 40 Gy/s as compared to 0.01 Gy/s in a conventional radiotherapy mode. In clinical linear accelerators (LINACs), the feedback mechanisms are based on averaged readouts over extended periods of time (for example 50 ms. in Varian LINACs). This feedback mechanism is too slow for FLASH therapy dose rates.

In embodiments, system 100 uses real-time feedback control. Particle source controller 110 includes a feedback controller that reads one or a plurality of inputs through, and running totals of radiation dose from, dosimetry controller 111; dosimetry controller 111 gets this information from various sensors including dosimeter 108 and Cherenkov cameras of cameras 120 that monitor the position and intensity of beam 104, and the treatment condition of the patient. Based on the one or plurality of inputs, particle source controller 110 may gate an upcoming pulse from particle source 102 off. In an embodiment, a total dose accumulator is found in dosimetry controller 111. In other embodiments, these sensors include a fast motion management system. In further embodiments, both sensors may be used in system 100.

Method of Pulse Modulation to Increase Absolute Dose Accuracy

Current beam monitor dosimeters are either not useful in high dose rate regimes due to strong non-linearity and/or signal to noise issues, they may experience dose-induced damage when subjected to ultra-high dose rate beams, or they are not fast enough to react on single pulse, millisecond basis.

A method to increase overall dose accuracy of FLASH particle beam delivery is disclosed herein. A prescribed total radiation dose of a FLASH therapy treatment is typically delivered in as a beam of a series of charged particle pulses. In embodiments, approximately 2 to 100 pulses may be delivered in a FLASH therapy session. Each charged particle pulse has a prescribed single pulse radiation dose less than the prescribed total radiation dose. Depending on the prescribed total radiation dose and the number of pulses used to deliver the prescribed total radiation dose, there may arise some situations in which a last pulse in the series would deliver too much radiation. This may occur, for example, if the prescribed total radiation dose is divided into a series of equal pulses, but some pulses delivered more radiation than intended due to variations within system 100.

In embodiments, the pulsewidth of an individual pulse of shaped beam 114 may be modulated to change the width or intensity of a single charged particle pulse. In order to maintain maximal dose rate throughout the treatment, a method that scales the pulsewidth (or duration) of the last charged particle pulse of the series based on a readout of dose per pulse accumulated through prior beam pulses by a total dose accumulator in dosimetry controller 111 that provides feedback to particle source controller 110. The total dose accumulator provides an accumulated radiation dose. It may be incorporated in particle source controller 110 or may be a separate device that communicates with particle source controller 110. Once a difference between the prescribed total radiation dose and the accumulated radiation dose reaches a value that is smaller than a prescribed single pulse dose, a scaling factor may be applied to the width and/or intensity of the subsequent, final, pulse. In this way, overall prescribed dose accuracy increases because beam output fluctuations during treatment accounted for.

In an embodiment, system 100 with scintillation dosimeters 108 and Cherenkov-light cameras in cameras 120 as described above is used with a beam measurement method, providing the total dose feedback data to particle source controller 110. In another embodiment, a FLASH-capable ionization chamber measure the beam output. For example, a typical ionization chamber is a gas-filled chamber in which high-energy (ionizing) radiation creates free charges that can be detected and whose rate of appearance corresponds to the intensity of high-energy radiation within the ionization chamber. The term "ionization chamber" is often applied to denote entire radiation-probe systems that include an ionization chamber, not only to the chamber per se. Ionization chamber probes are generally give a precise and highly localized measure of the ionizing radiation delivered by a therapeutic system at a given point, e.g., a point within a water-filled phantom. In particular embodiments, an ionization chamber is a cylindrical, waterproof Farmer-type ion ionization chamber, which is recommended by various dosimetry protocols for dose measurement of radiotherapy beams. The chambers of such probes typically have volumes of 0.6-0.65 cm3 and can report measured calibrated exposure accurate to National Institute of Standards & Technology (NIST) certified standards, which can be directly mapped to dose delivery at that point.

In an alternative embodiment, dosimetry is also performed by imaging Cherenkov radiation emitted as charged particles of the radiation beam that are moving at velocity less than the speed of light in a vacuum but faster than the speed of light in tissue slow to below the speed of light in tissue. In these embodiments, dosimetry controller 111 is configured to use images of Cherenkov radiation emitted by tissue of the patient to map and/or totalize radiation dose administered to the patient, to compare the mapped radiation dose administered to the patient to limits of a treatment plan and provide feedback to controller 110.

Whether measured by pre-collimator scintillation dosimeters as described above, by ionization chambers as described above, by imaging Cherenkov radiation, or a combination of two or more of the three, accurate run-time dosimetry permits automatic cessation of treatment and adjustment of width or intensity of final beam pulses to avoid exceeding radiation doses specified in the treatment plan.

System for Camera-Based Motion Management

In embodiments, FLASH therapy delivers the radiation dose of an entire conventional therapy session with a single fraction lasting less than a second, however, this imposes new and extreme requirements from the aspects of safety and patient positioning. In standard fractionated delivery, positioning, motion, or anatomy change errors are usually accounted for during planning and tend to average out over multiple days of treatment. However, a small deviation in patient position during FLASH therapy may have an impact on a patient's health that is orders of magnitude more severe. Anatomical shifts that may occur anytime between patient alignment and the end of beam delivery include shifts due to a non-compliant patient, inadvertent movement, and breathing motions of the patient, for example.

As shown in FIG. 1, one or several cameras 120 may be placed in locations with a view 122 of the treated area of a patient. Target fiducials 124 may be placed on the patient's skin prior the treatment to permit tracking of patient and tumor positions. Images of these fiducials are compared with planned fiducial locations in real time in order to detect motions of the patient and to gate the beam off if the detected position of the fiducials and treated area deviates from a planned treated area by more than a prescribed distance. In an embodiment, placement of target fiducial 124 may be performed as a part of treatment planning with anatomical guidance and pre-treatment X-ray computed tomography or magnetic resonance imaging images, and the cameras may observe absolute motion of the fiducials. In another embodiment, target fiducials 124 are placed immediately before treatment without anatomical guidance, and the motion is monitored relatively from the time of patient setup throughout the treatment. Deviation of the position of target fiducials 124 that is detected by cameras 120 may be provided to dosimetry controller 111 and used to control particle source controller 110 to control particle source 102 to gate off beam 104. Cameras 120 may work in visible and/or infrared light spectrum, the latter being useful to minimize perception by eyes. Target fiducials 124 may be reflective or fluorescent, and may be taped, tattooed, or inked onto patient skin. In some embodiments, cameras 120 configured to image fiducials are stereoscopic camera pairs and fiducial movement is observed and compared to limits in three dimensions.

In embodiments, one or more cameras 120 may work in 2D, sensitive only to motion along the imaging plane, or a plurality of cameras 120 may be used to evaluate a motion vector in 3D. The camera tracking and decision-making process happens within the time between two radiation pulses of beam 104, permitting near-instantaneous beam shutdown of excess movement is detected. In embodiments, this time may be approximately one or a few milliseconds.

The camera system as disclosed herein provides for absolute position monitoring and fast millisecond imaging and gating.

System for Cherenkov Camera-Based Motion Management

In embodiments, cameras 120 may also include the capability of detecting and imaging Cherenkov and/or scintillation emission from tissue. Further, the relation between the detected shape and location of the Cherenkov/scintillation area may be evaluated against the location of target fiducials 124. Biomarkers, such as the more attenuated blood vessel structures in Cherenkov/scintillation images, may in some embodiments be extracted and analyzed for motion tracking and used as additional fiducials. Beam 104 may be gated off if these relations, expressed in terms of spatial mismatch, exceed a predefined value specified in the treatment plan.

System for Optimized Dose Rate Distribution Delivery Through Intensity-Modulated Scanning In embodiments, beam scanning coil 116 and pulse modulation provided by total dose accumulation may be used together to optimally maximize the FLASH therapy efficacy. In particular, combining these elements of feedback and beam control provides the spatiotemporal intensity-modulation for optimizing both dose and dose rate distributions. A combination of the electromagnetic beam steering system as previously discussed with reference to beam dump 10, and the pulse modulation method as described above, enables the scanning of charged particle (electron and proton) beams with pulse-to-pulse intensity and position modulation. In embodiments, the system for ultra-high dose rate irradiation described herein may deliver dose and dose rate-optimized FLASH-RT plans through intensity-modulated scanning.

Figure 3:
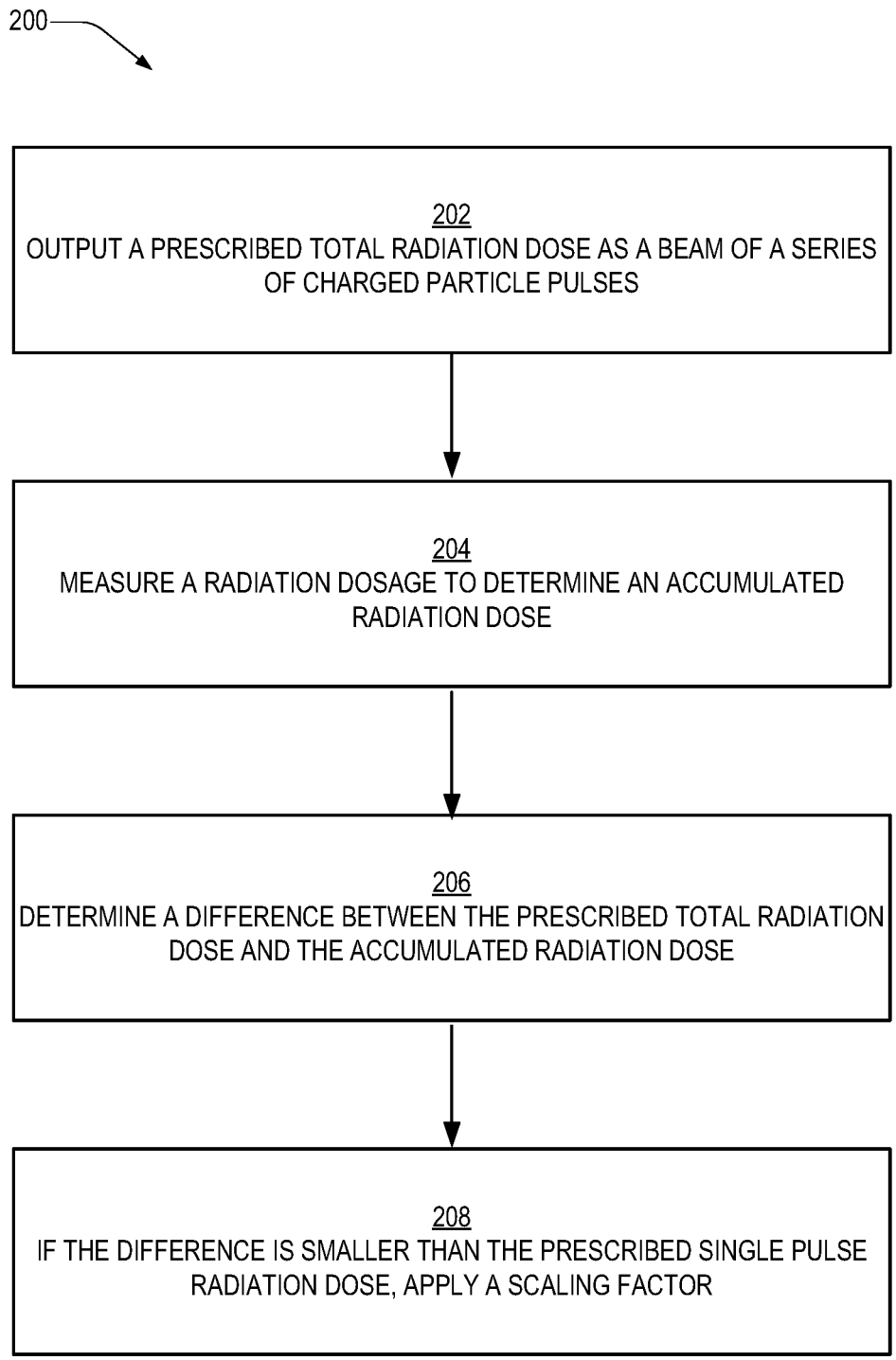
FIG. 3 is a flowchart of a method for delivering ultra-high dose rate irradiation therapy, in embodiments

FIG. 3 depicts a flowchart of a method 200 of providing ultra-high dose rate irradiation to a target area of a patient.

Step 202 includes outputting a prescribed total radiation dose a beam of a series of charged particle pulses. In an example of step 202, particle source 102 outputs a beam of a series of charged particle pulses to the target area of the patient. Each charged particle pulse has a prescribed single pulse radiation dose less than the prescribed total radiation dose.

Step 204 includes measuring a radiation dose to determine an accumulated radiation dose. In an example of step 204, a radiation dose provided by each charged particle pulse in the series is measured by dosimeter 108 and communicated to a total dose accumulator in dosimetry controller 110 to determine an accumulated radiation dose.

Step 206 includes determining a difference between the prescribed total radiation dose and the accumulated radiation dose. In an example of step 206, any charged particle pulse in the series may vary from the prescribed single pulse radiation dose, leading to a situation where only a partial dose should be applied in the last charged particle pulse. This situation is identified by accumulating the radiation dose from each charged particle pulse and comparing the accumulated total with the prescribed total radiation dose.

Step 208 includes, if the difference is smaller than the prescribed single pulse radiation dose, applying a scaling factor. In an example of step 208, a scaling factor may be applied to a width or an intensity of a subsequent charged particle pulse as described above.

Combination of Features

Features described above as well as those claimed below may be combined in various ways without departing from the scope hereof. The following enumerated examples illustrate some possible, non-limiting combinations:

(A1) A system for delivering ultra-high dose rate irradiation to a target area of a patient, comprising: a charged-particle source for providing a beam of radiation in a series of pulses along a beam axis; a collimator for shaping the beam of radiation into a shaped beam; one or more cameras for imaging the target area of the patient; and a controller for providing control signals to the charged-particle source; one or more dosimeters positioned in a beam fringe between an output of the charged-particle source and the collimator along the beam axis for measuring a radiation dosage provided by each pulse; and a beam scanning coil positioned between the collimator and the patient for directing the shaped beam; wherein the controller receives feedback from the one or more dosimeters and provides control signals to the particle source and the beam scanning coil that modulate each pulse in the series of pulses in real-time.

(A2) In system (A1), wherein the dosimeters further comprise one or more scintillators.

(A3) In system (A2), wherein the one or more scintillators further comprise an optical liquid cell filled with a liquid scintillator solution.

(A4) In system (A2), wherein one or more of the one or more scintillators is positioned in an outer region of the beam of radiation relative to the beam axis that is not used for treatment.

(A5) In any of systems (A1-A4), further comprising a total dose accumulator for receiving feedback from the one or more dosimeters during each pulse of the series of pulses.

(A6) In any of systems (A1-A5), further comprising a beam dump for receiving a beam diverted by the beam scanning coil; where the controller is configured to operate the beam scanning coil to divert the beam into the beam dump during an initial phase of beam output from the particle source.

(A7) In any of systems (A1-A6), further comprising one or more target fiducials placed in a target area for receiving the beam of radiation, wherein the one or more cameras observe the target area and the one or more target fiducials and provide feedback of patient motion to the controller.

(A8) In any of systems (A1-A7), wherein the one or more cameras are capable of imaging Cherenkov or scintillation emission from tissue of the patient.

(A9) In system (A8), wherein the cameras comprise cameras configured to image Cherenkov emission from tissue of the patient and the controller comprises a processor configured to map radiation dose administered of the patient from the images.

(B1) A method of providing ultra-high dose rate irradiation to a target area of a patient, comprising outputting a prescribed total radiation dose to the target area of the patient as a beam of a series of charged particle pulses from a particle source, each charged particle pulse having a prescribed single pulse radiation dose less than the prescribed total radiation dose; measuring a radiation dosage provided by each charged particle pulse in the series to determine an accumulated radiation dose; determining a difference between the prescribed total radiation dose and the accumulated radiation dose; and if the difference is smaller than the prescribed single pulse radiation dose, applying a scaling factor to a width or an intensity of a subsequent charged particle pulse.

(B2) In system (B1), wherein applying a scaling factor further comprises changing a duration of the subsequent charged particle pulse.

(B3) In either of systems (B1) or (B2), wherein applying a scaling factor further comprises controlling a beam scanning coil to change a width of the subsequent charged particle pulse.

(B4) In system (B3), further comprising controlling the beam scanning coil to divert the charged particle pulses into a beam dump during an initial phase of output from the particle source.

(B5) In any of systems (B1-B4), wherein providing a prescribed total radiation dose further comprises shaping the beam using a collimator.

(B6) In system (B5), wherein measuring a radiation dosage further comprises:

positioning one or more scintillators between a beam output of the particle source and the collimator along a beam axis between the particle source and the patient, wherein the one or more scintillators are positioned in an outer region of the beam relative to the beam axis that is not used for treatment of the patient; and reading light emissions of the one or more scintillators to determine the radiation dosage.

(B7) In any of systems (B1-B4), wherein measuring a radiation dosage further comprises imaging Cherenkov emissions from tissue of the patient and mapping radiation dose administered to tissue of the patient therefrom.

Changes may be made in the above methods and systems without departing from the scope hereof. It should thus be noted that the matter contained in the above description or shown in the accompanying drawings should be interpreted as illustrative and not in a limiting sense. Herein, and unless otherwise indicated: (a) the adjective "exemplary" means serving as an example, instance, or illustration, and (b) the phrase "in embodiments" is equivalent to the phrase "in certain embodiments," and does not refer to all embodiments. The following claims are intended to cover all generic and specific features described herein, as well as all statements of the scope of the present method and system, which, as a matter of language, might be said to fall therebetween.

What is claimed is:

1. A system for delivering ultra-high dose rate irradiation to a target area of a patient, comprising:
    a charged-particle source for providing a beam of radiation in a series of pulses along a beam axis;
    a collimator for shaping the beam of radiation into a shaped beam;
    one or more cameras for imaging the target area of the patient;
    at least one controller for providing control signals to the charged-particle source;
    one or more dosimeters positioned in fringes of the beam between an output of the charged-particle source and the collimator for measuring a radiation dosage provided by each pulse and provide signals to the at least one controller; and
    a beam scanning coil positioned between the collimator and the patient for directing the shaped beam;
    wherein the at least one controller provides control signals to the charged-particle source and the beam scanning coil that modulate each pulse in the series of pulses in real-time;
    wherein the one or more dosimeters further comprise one or more scintillator dosimeters; and
    wherein the one or more scintillator dosimeters further comprise an optical liquid cell filled with a liquid scintillator solution.

2. The system of claim 1, wherein one or more of the one or more scintillator dosimeters is positioned in an outer region of the beam of radiation relative to the beam axis that is not used for treatment.

3. The system of claim 1, further comprising a total dose accumulator for receiving feedback from the one or more dosimeters during each pulse of the series of pulses.

4. The system of claim 1, wherein the one or more cameras are capable of imaging Cherenkov or scintillation emission from tissue of the patient.

5. A system for delivering ultra-high dose rate irradiation to a target area of a patient, comprising:
    a charged-particle source for providing a beam of radiation in a series of pulses along a beam axis;
    a collimator for shaping the beam of radiation into a shaped beam;
    one or more cameras for imaging the target area of the patient at least one controller for providing control signals to the charged-particle source;
    one or more dosimeters positioned in fringes of the beam between an output of the charged-particle source and the collimator for measuring a radiation dosage provided by each pulse and provide signals to the at least one controller; and
    a beam scanning coil positioned between the collimator and the patient for directing the shaped beam;
    wherein the at least one controller provides control signals to the charged-particle source and the beam scanning coil that modulate each pulse in the series of pulses in real-time;
    further comprising:
    a beam dump for receiving a beam diverted by the beam scanning coil;
    where the at least one controller is configured to operate the beam scanning coil to divert the beam into the beam dump during an initial phase of beam output from the charged-particle source.

6. The system of claim 5, wherein the one or more cameras are capable of imaging Cherenkov or scintillation emission from tissue of the patient.

7. The system of claim 6, wherein the cameras comprise cameras configured to image Cherenkov emission from tissue of the patient and the at least one controller comprises a processor configured to map radiation dose administered to the patient from the images.

8. A system for delivering ultra-high dose rate irradiation to a target area of a patient, comprising:
    a charged-particle source for providing a beam of radiation in a series of pulses along a beam axis;
    a collimator for shaping the beam of radiation into a shaped beam;
    one or more cameras for imaging the target area of the patient at least one controller for providing control signals to the charged-particle source;
    one or more dosimeters positioned in fringes of the beam between an output of the charged-particle source and the collimator for measuring a radiation dosage provided by each pulse and provide signals to the at least one controller; and
    a beam scanning coil positioned between the collimator and the patient for directing the shaped beam;
    wherein the at least one controller provides control signals to the charged-particle source and the beam scanning coil that modulate each pulse in the series of pulses in real-time;
    further comprising:
    one or more target fiducials placed in a target area for receiving the beam of radiation, wherein the one or more cameras observe the target area and the one or more target fiducials and provide feedback of patient motion to the controller.

9. The system of claim 8 wherein the one or more cameras are capable of imaging Cherenkov or scintillation emission from tissue of the patient.

10. The system of claim 9, wherein the one or more cameras comprise cameras configured to image Cherenkov emission from tissue of the patient and the controller comprises a processor configured to map radiation dose administered to the patient from the images.

11. A method of providing ultra-high dose rate irradiation to a target area of a patient, comprising:

outputting a prescribed total radiation dose to the target area of the patient as a beam of a series of charged particle pulses from a particle source, each charged particle pulse having a prescribed single pulse radiation dose less than the prescribed total radiation dose;

measuring a radiation dosage provided by each charged particle pulse in the series to determine an accumulated radiation dose;

determining a difference between the prescribed total radiation dose and the accumulated radiation dose; and if the difference is smaller than the prescribed single pulse radiation dose, applying a scaling factor to a width or an intensity of a subsequent charged particle pulse;

wherein applying a scaling factor further comprises controlling a beam scanning coil to change a width of the subsequent charged particle pulse;

further comprising controlling the beam scanning coil to divert the charged particle pulses into a beam dump during an initial phase of output from the particle source.

12. The method of claim 11, wherein applying a scaling factor further comprises changing a duration of the subsequent charged particle pulse.

13. The method of claim 11, wherein providing a prescribed total radiation dose further comprises shaping the beam using a collimator.

14. The method of claim 13, wherein measuring a radiation dosage further comprises:

positioning one or more scintillators between a beam output of the particle source and the collimator along a beam axis between the particle source and the patient, wherein the one or more scintillators are positioned in an outer region of the beam relative to the beam axis that is not used for treatment of the patient; and reading light emissions of the one or more scintillators to determine the radiation dosage.

15. The method of claim 14 wherein measuring a radiation dosage further comprises: imaging Cherenkov emissions from tissue of the patient and mapping radiation dose administered to tissue of the patient therefrom.

16. The method of claim 11, wherein measuring a radiation dosage further comprises:

imaging Cherenkov emissions from tissue of the patient and mapping radiation dose administered to tissue of the patient therefrom.

17. The method of claim 16 wherein mapped radiation dose from Cherenkov images and radiation dose from scintillation dosimeters are recorded in a patient database.

* * * * *